United States Patent [19]

Warriner

[11] Plant 4,649

[45] Feb. 17, 1981

[54] ROSE PLANT

[75] Inventor: William A. Warriner, Tustin, Calif.

[73] Assignee: Jackson & Perkins Co., Medford, Oreg.

[21] Appl. No.: 90,660

[22] Filed: Nov. 2, 1979

[51] Int. Cl.[3] ..... A01H 5/00

[52] U.S. Cl. ..... Plt./17

[58] Field of Search ..... Plt./17

*Primary Examiner*—Robert E. Bagwill

*Assistant Examiner*—James R. Feyrer

*Attorney, Agent, or Firm*—Klarquist, Sparkman, Campbell, Leigh, Hall & Whinston

[57] ABSTRACT

Rose plant of hybrid tea class from cross of South Seas, U.S. Plant Pat. No. 2,184 with Tonight, U.S. Plant Pat. No. 3,522. Plant is similar in growth to South Seas with leaves of five or seven leaflets. Blossom color more intense than South Seas, being close to RHS 34A.

1 Drawing Figure

1

This present invention relates to a new and distinct variety of rose plant of the hybrid tea class which was originated by me by crossing the variety, South Seas, U.S. Plant Pat. No. 2,184, with pollen of the variety, Tonight, U.S. Plant Pat. No. 3,522.

The primary objective of this breeding was to produce a new rose variety of the hybrid tea class similar to the parent, South Seas, but with more intense color. This objective was substantially achieved along with other desirable improvements as evidenced by the following unique combination of characteristics which are outstanding in the new variety and which distinguish it from its parents as well as from all other varieties of which I am aware:

1. An upright plant similar in habit to the seed parent, South Seas.
2. A uniform flower color very close to The RHS Colour Chart #34A.
3. Large, brown prickles, angled slightly downward.
4. A very slight fragrance.
5. Leaves of five or seven leaflets.

Asexual reproduction of this new variety by budding as performed at Wasco, Calif., shows that the foregoing characteristics and distinctions are established and are transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:
- *Seed parent.*—South Seas.
- *Pollen parent.*—Tonight.

Classification:
- *Botanical.*—Rosa hybrid.
- *Commercial.*—Hybrid Tea.

FLOWER

Observations made from specimens grown outside at Irvine, Calif., in May, 1979.

Blooming habit: Continuous.

2

Bud:
- *Size.*—1" to 1⅛" when petals start to unfurl.
- *Form.*—Pointed ovoid, broad base.
- *Color.*—When sepals first divide, near RHSCC 47A, except inside of petals and where petal edges are turned over the color is near RHSCC 34A; when half blown, upper side of petals RHSCC 34A; lower side of petals between RHSCC 34A and RHSCC 47A.
- *Sepals.*—Color: Outer surface mostly RHSCC 187A; inner surface whitish tomentum; three appendaged sepals lightly appendaged; two unappendaged sepals hairy edged.
- *Receptacle.*—Color: RHSCC 138A. Shape: Wide funnel. Size: Broad. Surface: Smooth.
- *Peduncle.*—Length: Medium. Surface: Smooth. Color: RHSCC 187A. Strength: Stiff, erect.
- *Opening.*—Petals fall outward without quilling.

Bloom:
- *Size.*—Large. Average open size 4½".
- *Borne.*—Singly.
- *Stems.*—Long, strong.
- *Form.*—When first open, high centered. Permanence: Retains its form to the end.
- *Petalage.*—Number of petals under normal conditions: 30–35.
- *Color.*—Center of flower: Upper side of petals RHSCC 34A. Reverse side of petals between RHSCC 34A and 47A. Base of petals RHSCC 34A. General tonality from a distance: RHSCC 34A.
- *Variegations.*—None.
- *Discoloration.*—General tonality at end of first day, RHSCC 34B; third day, RHSCC 34C.
- *Fragrance.*—Slight.

Petals:
- *Texture.*—Thick.
- *Shape.*—Round.
- *Form.*—Tips slightly recurved.
- *Arrangement.*—Irregular. Petaloids in center, few.
- *Persistence.*—Drop off cleanly.
- *Lastingness.*—On the plant, long. As cut flower, long.

Reproductive parts:
- *Anthers.*—Large, many. Color, yellow. Arrangement, regular around styles.
- *Filaments.*—Color: Yellow.
- *Pollen.*—Gold yellow.

*Styles.*—Color: Reddish.
*Stigmas.*—Color: White.

PLANT

Form: Bush.
Growth: Very vigorous, upright; Grows normally to 6′ at Irvine, Calif.
Foliage: Number of leaflets on normal mid-stem leaves: 5 or 7.
*Size.*—Large.
*Quantity.*—Normal.
*Color.*—New foliage: Near RHSCC 187A. Old foliage: Near RHSCC 131A.
Leaflets:
*Shape.*—Oval pointed.
*Texture.*—Glossy.
*Edge.*—Serrated.
*Serration.*—Single, large.
*Petiole.*—Rachis: Color, green, Underside: Prickles.
*Stipules.*—Long, bearded.

*Disease resistance.*—Susceptible to mildew under normal growing conditions at Irvine, Calif.
Wood:
*New wood.*—Color: Bronzy brown. Bark: Smooth.
*Old wood.*—Color: Dark green. Bark: Smooth.
Prickles:
*Quantity.*—On main stalks from base, many. On laterals from stalk, many.
*Form.*—Long, hooked slightly downward.
*Color when young.*—Brown.
*Position.*—Irregular.
Small prickles:
*Quantity.*—On main stalks, none. On laterals, none.

I claim:

1. A new and distinct variety of rose plant of the hybrid tea class, substantially as herein shown and described, characterized particularly as to novelty by the unique combination of its vigorous, upright plant, blossom color of RHSCC 34A, large brown prickles, slight fragrance and tendency to develop leaves of five or seven leaflets.

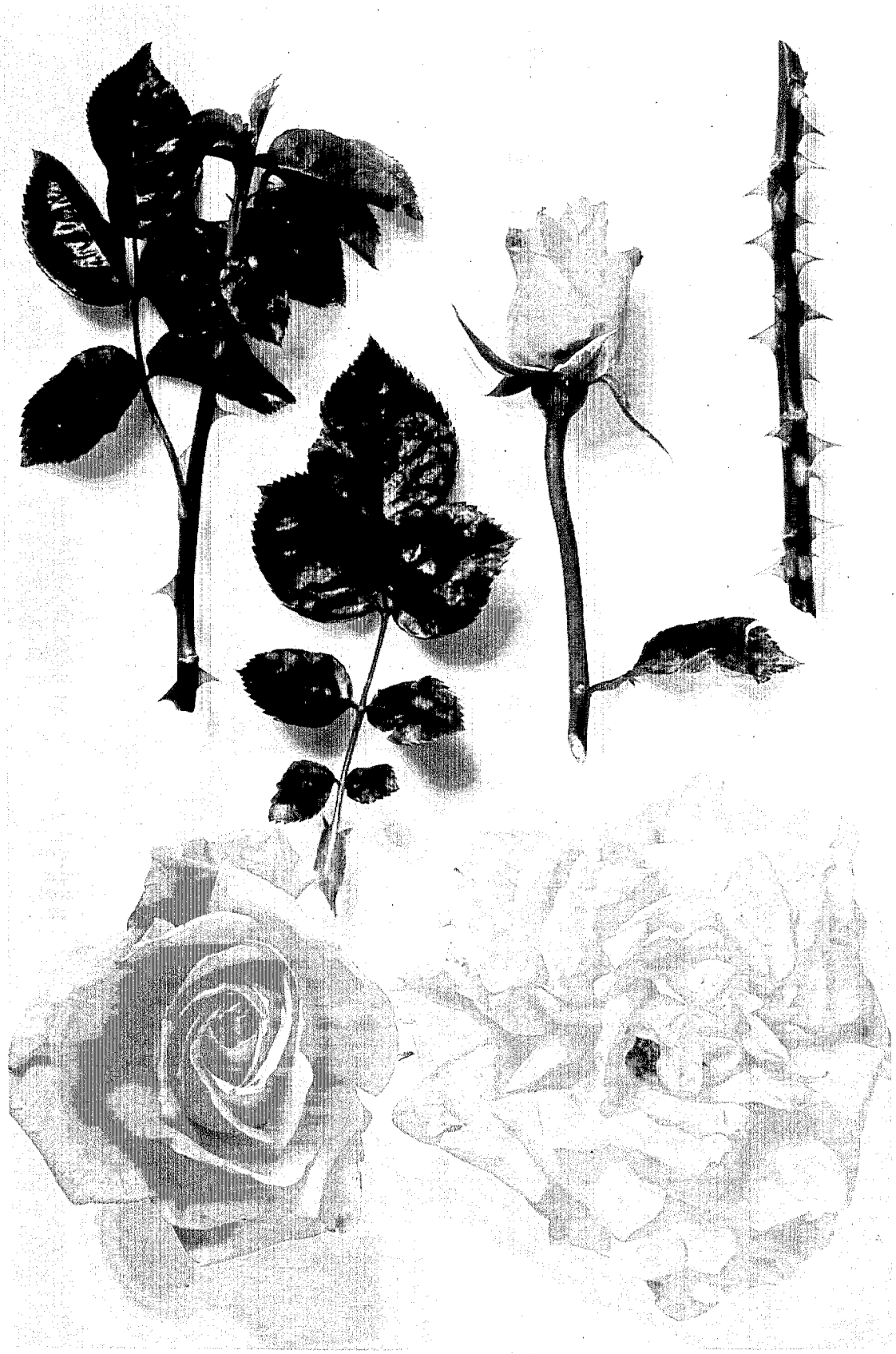

* * * * *